(12) United States Patent
Walbroel et al.

(10) Patent No.: US 8,623,427 B2
(45) Date of Patent: Jan. 7, 2014

(54) PLANT EXTRACTS FOR TREATING NEURODEGENERATIVE DISEASES

(75) Inventors: Bernd Walbroel, Königswinter (DE); Björn Feistel, Andernach (DE); Jens Pahnke, Rostock (DE)

(73) Assignee: Finzelberg GmbH & Co. KG, Andernach (DE)

( * ) Notice: Subject to any disclaimer, the term of this patent is extended or adjusted under 35 U.S.C. 154(b) by 0 days.

(21) Appl. No.: 13/517,381

(22) PCT Filed: Dec. 22, 2010

(86) PCT No.: PCT/EP2010/070531
§ 371 (c)(1),
(2), (4) Date: Jul. 31, 2012

(87) PCT Pub. No.: WO2011/076867
PCT Pub. Date: Jun. 30, 2011

(65) Prior Publication Data
US 2013/0022693 A1    Jan. 24, 2013

(30) Foreign Application Priority Data
Dec. 23, 2009   (EP) ..................................... 09180627

(51) Int. Cl.
*A01N 65/00*    (2009.01)
(52) U.S. Cl.
USPC ....................................................... 424/725
(58) Field of Classification Search
None
See application file for complete search history.

(56) References Cited

U.S. PATENT DOCUMENTS

| | | | |
|---|---|---|---|
| 6,322,824 | B1 | 11/2001 | Chatterjee et al. |
| 2002/0150637 | A1 | 10/2002 | Castillo et al. |

FOREIGN PATENT DOCUMENTS

| | | |
|---|---|---|
| DE | 10 2004 032165 A1 | 2/2006 |
| JP | 04-210642 A | 7/1992 |
| WO | 99/40905 A2 | 8/1999 |
| WO | 00/57707 A1 | 10/2000 |

OTHER PUBLICATIONS

Chow et al., "Potential cognitive enhancing and disease modification effects of SSRIs for Alzheimer's disease," Neuropsychiatric Disease and Treatment 3(5): 627-636 (2007).
Lehr et al., "Population pharmacokinetic modelling of NS2330 (tesofensine) and its major metabolite in patients with Alzheimer's disease," British Journal of Clinical Pharmacology 64(1): 35-48 (2007).
Marks et al, "Triple Reuptake Inhibitors: A Premise and Promise," Psychiatry Investigation 5: 142-147 (2008).
Nitsch et al., "Serotonin 5-HT2a and 5-HT2c Receptors Stimulate Amyloid Precursor Protein Ectodomain Secretion," The Journal of Biological Chemistry 271(8): 4188-4194 (1996).
Pákáski et al., "Imipramine and citalopram facilitate amyloid precursor protein secretion in vitro," Neurochemistry International 47: 190-195 (2005).
Third Party Observations from European Patent Application No. 10 800 741.0 (regional phase of PCT/EP2010/070531), dated Jul. 29, 2013.
Brookmeyer et al., "Forecasting the global burden of Alzheimer's Disease," Johns Hopkins University, Department of Biostatistics Working Papers, Paper 130 (2007).
Bu, "Apolipoprotein E and its receptors in Alzheimer's disease: pathways, pathogenesis and therapy," Nat Rev Neurosci, 10(5):333-344 (May 2009).
Corder et al., "Gene dose of apolipoprotein E type 4 allele and the risk of Alzheimer's disease in late onset families," Science (New Series), 261(5123):921-923 (Aug. 13, 1993).
Dekosky et al., "Ginkgo biloba for Prevention of Dementia: A Randomized Controlled Trial," JAMA, 300 (19):2253-2262 (2008).
Johne et al., "Interaktionen zwischen Phytopharmaka und anderen Arzneimitteln: Das Beispiel Johanniskraut (Interactions between herbal medicines and other drugs: The case for St. John's wort)," Bundesgesundheitsbl—Gesundheitsforsch—Gesundheitsschutz. 46:1061-1067 (Dec. 2003) (see English abstract on p. 1062).
Knörle et al.,"Extrakte aus *Sideritis* ssp. (griechischer Bergtee): Innovative zentral aktive Pflanzenextrakte mit breitem Wirkprofil (Extracts from *Sideritis* ssp. (Greek mountain tea): Innovative plant extracts acting on the central nervous system and having a broad activity profile)" http://ibam.de/pics/Poster-Wolnzach-2009.pdf (viewed Jul. 8, 2010).
Kumar et al., "Effect of Indian *Hypencum perforatum* Linn on animal models of cognitive dysfunction," Journal of Ethnopharmacology, 72:119-128 (2000).
Moore et al., "St. John's wort induces hepatic drug metabolism through activation of the pregnancy X receptor," Proc Natl Acad Sci USA, 97(13):7500-7502 (Jun. 20, 2000).
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," J Neurosci; 26(40): 10129-10140 (Oct. 4, 2006).
Pahnke et al., "Clinico-Pathologic Function of Cerebral ABC Transporters—Implications for the Pathogenesis of Alzheimer's Disease," Current Alzheimer Research, (4)396-405 (2008).
Pahnke et al., "Alzheimer's disease and blood-brain barrier function—Why have anti-β-amyloid therapies failed to prevent dementia progression?," Neurosci Biobehav Rev., 33(7):1099-1108 (Jul. 2009).

(Continued)

*Primary Examiner* — Michael Meller
(74) *Attorney, Agent, or Firm* — Dardi & Herbert, PLLC; Peter S. Dardi

(57) ABSTRACT

The invention relates to the use of bedstraw extracts that can be obtained by means of extracting using water or water-alcohol solvents or mixtures thereof, for producing a formulation, and for treating or preventing neurodegenerative diseases.

6 Claims, No Drawings

(56) References Cited

OTHER PUBLICATIONS

Silva et al., "Neuroprotective Effect of *H. perforatum* Extracts on β-Amyloid-induced Neurotoxicity," Neurotoxicity Research 6(2):119-130 (2004).

"Aktualisierungsrecherche zum Bericht A05-19A (Cholinesterasehemmer bei Alzheimer Demenz) (Update search on report A05-19A (Cholinesterase inhibitors in Alzheimer's disease))," IQWiG Reports No. 67, produced by the IQWiG (German Institute for Quality and Efficiency in Health Care) (2009).

Search Report for corresponding European Patent Application No. 09 18 0627 dated Aug. 9, 2010.

PLANT EXTRACTS FOR TREATING NEURODEGENERATIVE DISEASES

CROSS REFERENCE TO RELATED APPLICATIONS

This application is a national stage filing of PCT application number PCT/EP2010/070531 filed on Dec. 22, 2010, which claims priority to European patent application number 09180627.3 filed on Dec. 23, 2009, both of which are incorporated herein by reference.

FIELD OF THE INVENTION

The invention relates to plant extracts and their use.

BACKGROUND OF THE INVENTION

Neurodegenerative diseases with protein depositions comprise a wide range of clinical symptoms. They are characterized by pathologically abnormal, global or local concentrations of proteins or protein fragments (peptides) and deposits or aggregations triggered by them, which due to prior dimerization or oligomerization may result in ordered structures (e.g. fibrils) and which can even form crystalline protein structures (e.g. β-amyloid in Alzheimer plaques).

Diseases hiding behind this pathology include Huntington's chorea, in which Huntingtin accumulates and is deposited in core regions of the brain. Spinocerebellar ataxia type 2 (SCA2) is a neurodegenerative disease believed to be caused by the protein ataxin-2, which has been detected in an agglomerated form. In the case of Lewy body dementia (LBD), the agglomerated form of the protein α-synuclein can be determined pathophysiologically, which also brings together the clinical characteristics of Parkinson's disease and multiple-system atrophy (MSA) in the group of the "synucleinopathies". Another group of neurodegenerative diseases is formed by the tauopathies, in which the cytoskeletal protein tau protein clusters to fibrillar structures (PHFs or tangles).

A large group of such protein deposits can be observed with amyloidoses. Large quantities of abnormally modified proteins appear which are deposited as insoluble small fibres (fibrils). In the case of the amyloidoses, it is a perturbation in the folding of a normally soluble protein which is the underlying cause. These proteins congregate through abnormal concentrations to larger β-pleated sheet structures and eventually form fibrils.

As the fibrils are relatively resistant to the body's own defence mechanisms (phagocytosis and proteolysis), they cannot be completely removed from the organs affected. These deposits then destroy the architecture of the organs, the result of which is malfunctions and even total failure. Amyloidoses are a pathological deposition process which can be triggered by various metabolic disorders and which results in different chronic changes or diseases, depending on the organ affected.

A special manifestation of amyloidosis is amyloidosis of aging, which mainly affects the heart and brain. Today, this form is described immunohistochemically as AS-amyloidosis and is understood to mean all amyloid proteins which cause senile amyloidosis. Although the trigger proteins have not yet been characterized in many cases, frequent occurrence is associated with Alzheimer's disease.

Another peripheral degenerative disease with protein deposition is, for example, inclusion body myositis (IBM), where deposited molecules/peptides are found within muscle fibre which are associated with degenerative organ processes in other places as well, such as β-amyloids and prion protein. The latter is seen, inter alia, as the cause of the inflammatory muscle process with IBM.

Alzheimer's disease, also known as Alzheimer's dementia, presenile sclerosis as well as senile dementia-Alzheimer type, internationally abbreviated to AD, is a neurodegenerative disease which occurs in its most frequent form in people above the age of 65 and is believed to have been responsible for some 29 million cases of dementia in 2007. [R. Brookmeyer et al: Forecasting the global burden of Alzheimer's disease. In: Alzheimer's and Dementia. March/2007, vol. 3, pp. 186-191]. The cognitive skills deteriorate as the disease advances, which may lead to behavioural disorders and character changes. So-called plaques consisting of aggregated β-amyloid peptides (Aβ) may be found in the brains of those suffering from Alzheimer's. It has so far not been possible to find any definite cause for the disease's sporadic variant but genetic mutations on three different genes are thought to be associated with familial AD. Special allele genotypes of the apolipoprotein E (ApoE), and in particular of the ApoE4, are likewise thought to increase the risk of contracting AD. [Corder, E. H. et al. (1993): *Gene dose of apolipoprotein E type 4 allele and the risk of Alzheimer's disease in late onset families*. In: *Science* 261 (5123):921-923] [Bu, G. (2009): *Apolipoprotein E and its receptors in Alzheimer's disease: pathways, pathogenesis and therapy*. In: *Nat. Rev. Neurosci.* 10(5):333-344.]. Demographic developments with their rise in the average age of the population will also see an ever greater number of people developing AD in the next few decades. The prevalence of Alzheimer's increases from 2% in 65-year-olds to 20% in 85-year-olds. Forecasts for the year 2050 predict a prevalence heading towards over 100 million patients. This large number of patients will thus constitute a considerable burden for the population at large. Delaying the pathogenesis by approx. 5 years could not only postpone the individual suffering until the natural death but also substantially reduce the anticipated costs for the community as a whole.

So-called senile plaques and fibrillar tangles (NFTs) are found in the brain of Alzheimer patients upon closer observation of the pathogenetic mechanism. The protein deposits of the plaques consist mainly of amyloid-β peptides. The intracellular neurofibrillary tangles consist of the tau protein. This aggregates to fibrils if it phosphorylates more strongly than normal, i.e. is bound with phosphoric acid residues ("hyperphosphorylation"). It is uncertain whether this tau phosphorylation is secondary in nature or triggers the disease. Neurons dying off cause the cerebral mass to decrease as the disease progresses; this is then referred to as cerebral atrophy. In addition to this, the neurotransmitter acetylcholine is no longer produced in sufficient quantities, which leads to a general reduction in the performance of the brain.

The Aβ-peptides are formed from a precursor protein, the amyloid precursor protein (APP), which is an integral membrane protein. It is a type I transmembrane protein: its large amino terminal end is on the outside of the cell while a smaller carboxyl terminus can be found within the cell. APP is cleaved by proteolytic enzymes, the so-called secretases (α-secretase, β-secretase and γ-secretase), which can result in the Aβ-peptide being released from the precursor protein. There are basically two ways in which APP can be cleaved. The non-amyloidogenic way: APP is cleaved by an α-secretase. This cleavage takes place within the APP part containing the Aβ and it prevents Aβ forming. A large extracellular portion, whose function has not been definitively explained, is then released. The amyloidogenic way: APP is first cleaved by the β-secretase and then by the γ-secretase. This cleavage, which takes place within the transmembrane domain, results in Aβ being released. Both processes can occur at the same time in nerve cells. The Aβ-peptides formed by β- and γ-secretases vary in their length. The main type (Aβ-40) is 40, while a small portion (Aβ-42) is 42 amino acids long. The length of the Aβ is of central pathological importance because the longer Aβ-42 exhibits a considerably higher tendency to aggregation than the shorter Aβ-40.

There are genetic causes which lead to Alzheimer's disease. Approximately one to five percent of those affected exhibit a familial accumulation (familial Alzheimer's disease (FAD)), which can be attributed to mutations of the presenilin-1 gene on chromosome 14, of the presenilin-2 gene on chromosome 1 or of the APP gene on chromosome 21. Down's syndrome with its three copies of chromosome 21, upon which is the APP gene, also increases the risk of developing a form of dementia, possibly Alzheimer's disease. Psychodiagnostic detection in people with this genome mutation is made more difficult, however, by a cognitive impairment usually already present early on.

In the case of Alzheimer's disease, there is also a malfunction of the mitochondria. A blockage of the electron transport chain at Complex IV leads to excessive production of radicals which damage the cell. The question is still unsettled as to whether this blockage is a result of excessive Aβ production or whether Aβ is produced in excessive quantities as an antioxidant against this new oxidative stress. Antioxidative extracts can be used to prevent radical-triggered Aβ production if need be.

ABC transporters form a large family of membrane proteins which actively translocate specific substrates across a cell membrane. ABC transporters belong on the one hand to the primarily active transporters and on the other hand to the membranous ATPases. The ABC transporter superfamily comprises one of the largest known protein families with members in nearly every organism, from bacteria to plants and mammals. The ABC transporters have become a focus of attention in the last few years since it was realised that they are of considerable medical, industrial and economic significance. Tens of thousands of people die of cancer each year because chemotherapy has failed due to the strong expression of ABC transporters in tumour tissue. Mutations in a gene which codes for an ABC transporter can lead to various metabolic diseases in people. All eukaryotic ABC transporters are exporters. Some of them are highly substrate-specific while others are multi-specific. ABC transporters also translocate, inter alia, β-amyloid and are therefore regarded as part of the pathogenetic mechanism which leads to AD [Pahnke et al. 2008: Clinico-pathological function of cerebral ABC transporters—implications for the pathogenesis of Alzheimer's disease. Current Alzheimer Research 5, 396-406; Pahnke et al. 2009: Alzheimer's disease and blood-brain barrier function—Why have anti-β-amyloid therapies failed to prevent dementia progression? NeurosciBiobehavR 33:1099-1108].

SUMMARY OF THE INVENTION

The field of phytopharmaceuticals has produced many plant extracts which today are known for their CNS activity. It is necessary in such cases for ingredients of the plants to overcome the blood-brain barrier. Extracts for which CNS activity has been demonstrated in clinical studies are based on plants such as ginseng, ginkgo, passion flower, St John's wort, valerian, hop, lavender, green tea, sage and others.

Therapeutic agents approved for treating neurodegenerative dementia disorders, which include, for example, Alzheimer's disease (AD) and dementia caused by Parkinson's disease (PD), are currently used solely to treat the symptoms. The prevailing presumption in the case of dementia is that the clinical symptoms are caused by a lack of the neurotransmitter acetylcholine (ACh). A therapeutic approach is thus taken by trying to inhibit the enzyme responsible for breaking down acetylcholine (acetylcholinesterase inhibitors). These ACh inhibitors, such as donepezil or galantamine, are approved in Germany for the treatment of AD. The symptomatic therapies currently used are only able to delay progress of the disease to a limited extent, however; there can certainly not be any question of mitigation of the clinical picture at the moment.

A review carried out by the IQWiG (German Institute for Quality and Efficiency in Health Care) published in August 2009 [IQWiG reports—year: 2009 no. 67: Updating investigation for the report A05-19A (cholinesterase inhibitors in Alzheimer's disease)] comes to the conclusion that the three drugs donepezil, galantamine and rivastigmine approved in Germany can only slightly delay the decrease in cognitive powers in patients with mild to moderate Alzheimer's disease. The review also found evidence suggesting that these preparations may reduce the speed with which Alzheimer patients lose the ability to manage activities of daily living. A benefit in terms of the health-related quality of life was not proven and all three drugs showed significant side effects in some cases.

Extracts from Ginkgo biloba, which are meant to act prophylactically on dementia diseases and their advance, have so far not shown any degree of success in the treatment of neurodegenerative diseases with protein depositions. A current, large-scale, prospective, double-blind, placebo-controlled study with over 3,000 patients included was unable to demonstrate any effect with regard to reducing the number of new cases or slowing down the clinical progression of dementia disorders which had already begun to develop [DeKosky et al.; Ginkgo biloba for Prevention of Dementia: A Randomized Controlled Trial. *JAMA*. 2008; 300(19):2253-2262].

Plant extracts from St John's wort (*Hypericum perforatum* spp.) are known as CNS active extracts and are used as a "mood lifter" for mild to moderate depression. So-called total extracts from alcohol-water solutions are used here as the active pharmaceutical ingredient (API). Silva et al. [Neurotoxicity Research, 2004, vol. 6(2), pp. 119-130] describe a neuroprotective effect of a *hypericum* extract on β-amyloid-induced neurotoxicity. The extract described here, with 80% ethanol as the extractant, demonstrated good cytoprotective properties in vitro. However, this publication reveals both a toxic effect of a hyperforin fraction and a protective effect of the flavonoid fractions. Used worldwide for mild depression, St John's wort extracts have also been studied in quite some detail with regard to their potential side effects. It is in particular for hyperforin and extracts containing very high quantities of hyperforin that most of the reported cases of side effects have been verified, however. [Johne et al. (2003) BGBL 46:1061-1067/DOI 10.1007/s00103-003-0742-y] Dose-related side effects and interactions with cytochrome oxidases of the P450 system are likewise described [Moore et al. (2000) St John's wort induces hepatic drug metabolism through activation of the pregnane X receptor. Proc Natl Acad Sci USA 97:7500-7502]. These interactions lead to interactions with the metabolism of a series of approved drugs. Sporadic dementia illnesses appear at the age of over 60 years, a time in life when a large number of patients are already being treated with medicines for hyperlipaemia, hypertension and other effects of the metabolic syndrome.

The P450 side effects spectrum can be attributed in particular to the quantity of hyperforin in the extracts, while too high a concentration of hypericin is believed to be responsible for phototoxic side effects.

The task of the invention was to provide preparations which are suitable for treating neurological diseases—and in particular of the degenerative type—and to combine the best possible efficacy with a low potential for side effects.

The task is solved by using plant extracts selected from ironwort extracts which are obtained by means of extraction using water or water-alcohol solvents or mixtures thereof for producing a formulation for treating or preventing neurodegenerative diseases.

The subject matter of the invention is thus the use of extracts from plants of the family Lamioideae (ironwort plants).

Such extracts are produced from the superterranean parts of the ironwort using water or water-alcohol solvents.

Water-alcohol solvents means that they are mixtures of water and alcohols. The alcohol content preferably ranges from 10 to 90%. The information regarding the concentration of the alcohols is given in % (v/v) at 25°.

An extraction with water-alcohol solvents means that primary extraction from the drug is carried out with this solvent.

The extract preparations obtained are suitable for treating or preventing neurodegenerative diseases. Without being tied to this theory, it is suspected that the efficacy of the extracts might be produced by activation of the ABC transporters.

DETAILED DESCRIPTION OF THE INVENTION

Current publications of the applicants [Pahnke et al. 2008: Clinico-pathological function of cerebral ABC transporters—implications for the pathogenesis of Alzheimer's disease. Current Alzheimer Research 5, 396-406; Pahnke et al. 2009: Alzheimer's disease and blood-brain barrier function—Why have anti-β-amyloid therapies failed to prevent dementia progression? NeurosciBiobehavR 33:1099-1108] show that ABC transporters have an important function in the removal of protein deposits in people suffering from dementia, in particular β-amyloid deposits in the case of AD. These transporters are found at natural barriers, such as the blood-brain barrier. Activating these transporters, of which 49 human transporters are known, might lead to a reduction of intracerebral protein aggregates and peptide aggregates.

The subject matter of the invention is to prevent the pathological aggregation and accumulation of proteins in vivo by using plant extracts or extract combinations and to partly or completely dissolve protein accumulations already aggregated (also oligomers) and to then remove the degradation products from the brain/the organs. Ultimately both the concentration of toxic intermediates and the aggregation in the neurons can be reduced by the inventive use of plant extracts.

According to the invention the plant active substances will help to reduce both intra- and extraneuronal soluble and insoluble protein aggregates. Since many people suffering from dementia are likely to need long-term treatment to the end of their lives, well-tolerated substances with as few side effects as possible should ideally be used for a good benefit-risk relationship. Plant extracts are sufficiently well known from treating other disorders and diseases of the CNS for their good tolerance and low incidence of side effects.

The results show that there is also a reduction in the plaque count.

In EP 1 054 682 an in-vitro activity of hyperforin is described in a learning performance model which has been associated with dementia. In-house tests in vivo on mouse models of AD have surprisingly shown, however, that the activities of the St John's wort extracts tested had no correlation with the hyperforin content (see examples 2 and 3). Extracts low in hyperforin are particularly active, however, and what is more, the entire extract matrix—essentially determined by the extractant in the manufacturing process—explains the difference on mouse models of AD (see table, example 7).

Neurodegenerative diseases are in the main diseases which are associated with accumulated proteins or peptides, so-called neurodegenerative diseases with protein deposits.

The diseases may be Down's syndrome, Huntington's disease (HD), spinocerebellar ataxia (SCA), in particular SCA2, or amyloidoses, in particular Alzheimer's disease (AD).

In another variant the diseases may be synucleinopathies, in particular multiple-system atrophy (MSA), Parkinson's disease (PD), or Lewy body dementia (LBD).

In a further variant the diseases may be tauopathies, frontotemporal lobar degenerations/dementia (FTLD), amyotrophic lateral sclerosis (ALS), or inclusion body myositis (IBM).

The inventive extracts can also be used to treat development/early forms of a dementia disease, such as mild cognitive impairment (MCI) in Alzheimer's disease.

An extract is used in a variant of the invention which is obtained by extraction from St John's wort. St John's wort is described in the European Pharmacopoeia. It is the superterranean part of the *Hypericum perforatum*. 80 vol % aqueous ethanol has proved to be particularly good as an extractant.

In one variant the extract is produced from Herba *Sideritis* spp. It is in particular aqueous solvents and aqueous alcohol mixtures chosen from methanol, ethanol, 1-propanol or 2-propanol in quantities of 10 to 70% alcohol by volume that have been found to be preferable for *Sideritis* extracts. Particularly preferred are alcohol concentrations between 20 and 40% alcohol by volume.

The extracts obtained can be used in suitable preparations, in particular as tablets, tinctures, capsules, sachets, drinking ampoules or lozenges.

Native extract quantities of 300 mg to 1200 mg per day are especially suitable.

The inventive extracts can be used to produce a drug. It can, however, also be a foodstuff or a nutritional supplement or a supplementary balanced diet which is used to support drug treatment of the neurodegenerative disease.

The following examples illustrate the invention in greater detail.

Example 1

Test Model

The efficacy of the extracts tested was assayed in the following in-vivo model:

A genetically generated mouse strain with an Alzheimer's disease predisposition (see e.g. Oakley H. et al. 2006, Intraneuronal beta-amyloid aggregates, neurodegeneration, and neuron loss in transgenic mice with five familial Alzheimer's disease mutations: potential factors in amyloid plaque formation. J Neurosci 26(40):10129-40) generally develops the first deposits of β-amyloid from 1.5-2 months after birth. From day 50 the mice are gavage fed a dose of the extract each day. The animals are killed after a defined total lifetime of 75 or 100 days and their brains analysed. This involves molecular biological measurement of the concentration of the soluble Aβ42 fraction by means of ELISA. The number and the area are the parameters used to assay the plaque deposits histologically (mean values; n≥3).

Example 2

Comparative Example St John's Wort 80% EtOH Low in Hyperforin 10.7 kg St John's wort (Ph. Eur.) is macerated twice at 45° C. with 100 litres ethanol 80% (v/v). The eluate is liberated from suspended matter by filtration and gently concentrated to a soft extract. The extract obtained in this way was cooled down to 4° C. and a resin phase skimmed off its top after 8 hours. The remaining soft extract was dried and ground 70% native with 14% maltodextrin, 14% siliconized microcrystalline cellulose and with 2% highly dispersed silicon dioxide. This produced 4.5 kg of extract characterized by a content of 0.09% hypericin, of 0.3% hyperforin and of 5.7% flavonoids.

The extract obtained in this way was tested in the in-vivo model described in example 1. The results are given in example 7.

Example 3

Comparative Example St John's Wort 80% EtOH with the Usual Hyperforin Concentration 10 kg St John's wort (Ph. Eur.) is extracted exhaustively at 50° C. with 150 litres ethanol 80% (v/v). Once it has cooled down to room temperature, the eluate is liberated from suspended matter by filtration and gently concentrated to a soft extract. This extract was dried and ground 98% native with 2% highly dispersed silicon dioxide. This produced 2.2 kg of extract characterized by a content of 0.21% hypericin, of 2.9% hyperforin and of 11.3% flavonoids.

The extract obtained in this way was tested in the in-vivo model described in example 1. The results are given in example 7.

Example 4

Inventive Example from Herba *Sideritis scardica*

10 kg ironwort (*Sideritis scardica* L.) was percolated exhaustively at 50° C. with 300 litres ethanol 20% (v/v). The eluate was drained off from the drug and liberated from drug residues. The percolate was gently evaporated in a partial vacuum and all solvents removed by adding water several times. This yielded 4.2 kg of soft extract with a dry matter content of 43.3%. This was dried with the aid of maltodextrin in a ratio of 70% native:30% maltodextrin.

The extract obtained in this way was tested in the in-vivo model described in example 1. The results are given in example 7.

Example 5

Inventive Example from Herba *Sideritis euboa*

10 kg ironwort (*Sideritis euboa*) was percolated exhaustively at 50° C. with 300 litres ethanol 20% (v/v). The eluate was drained off from the drug and liberated from drug residues. The percolate was gently evaporated in a partial vacuum and all solvents removed by adding water several times. This yielded 3.9 kg of soft extract with a dry matter content of 42.6%. This was dried with the aid of maltodextrin in a ratio of 70% native:30% maltodextrin.

The extract obtained in this way was tested in the in-vivo model described in example 1. The results are given in example 7.

Example 6

Inventive Example from Herba *Sideritis* spp 10 kg ironwort (50/50 mixture of *Sideritis scardica* L. and *S. euboa* L.) was percolated exhaustively at 50° C. with 300 litres ethanol 20% (v/v). The eluate was drained off from the drug and liberated from drug residues. The percolate was gently evaporated in a partial vacuum and all solvents removed by adding water several times. This yielded 3.2 kg of soft extract with a dry matter content of 56%. This was dried with the aid of maltodextrin in a ratio of 70% native:30% maltodextrin.

The extract obtained in this way was tested in the in-vivo model described in example 1. The results are given in example 7.

Example 7

Results of the β-Amyloid Formation in the In-Vivo Test

The mouse strain examined in example 1 is changed in such a way that the amyloid deposits typical for Alzheimer's disease are distinct after approx. 100 days of life. Treatment commenced after 50 days of life.

|  | Quantity of soluble fraction Aβ42 (mean value in ng per mg total brain protein) | Period of treatment in days (age in days when analysed) |
|---|---|---|
| Control strain (H$_2$0 treatment) | 54.1 | 25 d (75 d) |
| *Hypericum* 80% EtOH low in hyperforin as in example 2 | 23.9 | 25 d (75 d) |
| *Hypericum* 80% EtOH rich in hyperforin as in example 3 | 35.3 | 25 d (75 d) |
| *Sideritis scardica* as in example 4 | 20.3 | 25 d (75 d) |
| *Sideritis euboa* as in example 5 | 18.3 | 25 d (75 d) |
| *Sideritis* spp. as in example 6 | 32.8 | 25 d (75 d) |

The *Sideritis* extracts as in examples 4-6 lower the soluble fraction of the β-amyloid compared with the control treatment with water. While *S. scardica* produced a reduction of the soluble Aβ42 fraction by 62.5%, *S. euboa* achieved a 66.2% reduction (n≥3). It was therefore possible to achieve a greater reduction of the soluble Aβ42 fraction than was obtained with the St John's wort extracts from EtOH 80%, which have been confirmed in the known literature (Silva, B. et al., Neurotoxicity Research 2004, 119-130) and thus as prior art with the test model used.

It is thus not an ingredient of the extract but the entire extract matrix—determined by the plant species used, the solvent in the production process—that is the decisive factor for the successful use of a *Sideritis* extract for neurodegenerative diseases.

Example 8

Histological Evaluation of the Plaque Formation

The mouse strain examined in example 1 is changed in such a way that the amyloid deposits typical for Alzheimer's disease are distinct after approx. 100 days of life. Treatment commenced after 50 days of life.

Dependence of the plaque formation on the duration of the treatment after administering 4000 mg/kg St John's wort extract as in example 2 ($n \geq 5$):

| Duration | 75 d | 100 d |
|---|---|---|
| Plaque Number (N) | | |
| Control group | 109.6 | 203.0 |
| St John's wort extract as in example 2 | 64.5 | 129.5 |
| Relative change | −41.1% | −36.2% |
| Mean plaque area (A in $\mu m^2$) | | |
| Control group | 380.6 | 498.0 |
| St John's wort extract as in example 2 | 337.4 | 367.5 |
| Relative change | −11.3% | −26.2% |

Example 9

Histological Evaluation of the Plaque Formation

As in example 8, the plaque formation was measured after administering *Sideritis* extracts.

Change in the plaque formation after administering 4000 mg/kg *Sideritis* extract as in example 6 ($n \geq 5$):

| Duration | 100 d |
|---|---|
| Plaque Number (N) | |
| Control group | 203.0 |
| *Sideritis* extract as in example 6 | 103.6 |
| Relative change | −49% |
| Mean plaque area (A in $\mu m^2$) | |
| Control group | 498.0 |
| *Sideritis* extract as in example 6 | 422.2 |
| Relative change | −15.2% |

With the plaque area approximately the same, the number has been reduced significantly.

Example 10

Inventive Example from Herba *Sideritis scardica*

10.1 kg ironwort (*Sideritis scardica* L.) was percolated exhaustively at 80° C. with 384 litres purified water. The eluate was drained off from the drug and liberated from drug residues by means of filtration through a cellulose filter (250 μm). The clear percolate was gently evaporated in a partial vacuum. This yielded 2.1 kg of soft extract with a dry matter content of 63.0%. This was formulated, pasteurized and vacuum dried at 55° C. with the aid of maltodextrin in a ratio of 70% native:30% maltodextrin. The extract obtained was ground through a 0.75 mm sieve to a homogeneous, brown powder.

The water-soluble powder is suitable for making sachets, instant drinking powder and effervescent tablets or for adding to soluble drinks.

Example 11

Tablet Formulation

One tablet contains 300 mg *Sideritis* dry extract as in example 6. Other ingredients are the disintegrator sodium carboxymethyl cellulose, the flow agent silicon dioxide, the binder polyethylene glycol 4000, the lubricant magnesium stearate, and sodium bicarbonate.

The invention claimed is:

1. A method of treating Alzheimer's disease in a patient in need thereof consisting essentially of administering therapeutically effective amounts of an ironwort extract and a St. John's wort extract to said patient, to treat said Alzheimer's disease in said patient.

2. The method of claim 1, wherein said ironwort extract has been prepared from *Sideritis* spp. Herb.

3. The method of claim 1 wherein the ironwort extract is in the form of a medicament, food, food supplement or supplementary balanced diet.

4. The method of claim 1 wherein the St. John's wort extract is prepared with 80% ethanol as extractant.

5. The method of claim 1, wherein said extract has been prepared from *Sideritis scardica* herb, *Sideritis euboa* herb or mixtures thereof.

6. The method of claim 1, wherein the ironwort extract is obtainable by extraction with water or aqueous-alcoholic solvents.

* * * * *